(12) United States Patent
Inoue et al.

(10) Patent No.: US 6,447,725 B1
(45) Date of Patent: Sep. 10, 2002

(54) TOTAL ORGANIC CARBON METER

(75) Inventors: Minako Inoue; Youzo Morita, both of Kyoto (JP)

(73) Assignee: Shimadzu, Corporation, Kyoto (JP)

( * ) Notice: Subject to any disclaimer, the term of this patent is extended or adjusted under 35 U.S.C. 154(b) by 0 days.

(21) Appl. No.: 08/434,295

(22) Filed: May 3, 1995

(30) Foreign Application Priority Data

May 27, 1994 (JP) .............................................. 6-138038

(51) Int. Cl.⁷ .............................................. G01N 31/12
(52) U.S. Cl. ........................ 422/80; 422/78; 422/82.05; 436/145; 436/146
(58) Field of Search .................. 422/78, 82.5, 80; 436/145, 146

(56) References Cited

U.S. PATENT DOCUMENTS

| | | | | |
|---|---|---|---|---|
| 4,095,951 A | * | 6/1978 | DiCola et al. ............... | 436/146 |
| 4,325,907 A | * | 4/1982 | Dembicki, Jr. et al. ....... | 422/80 |
| 4,352,673 A | * | 10/1982 | Espitalie et al. ......... | 23/230 EP |
| 4,569,918 A | * | 2/1986 | Moore et al. ................ | 436/122 |
| 4,619,902 A | * | 10/1986 | Bernard ...................... | 436/145 |
| 4,626,413 A | * | 12/1986 | Blades et al. ................ | 422/78 |
| 4,887,453 A | * | 12/1989 | Carter et al. ................ | 73/1 R |
| 4,939,921 A | * | 7/1990 | Carter et al. ................ | 73/1 R |
| 4,968,485 A | * | 11/1990 | Morita ........................ | 422/78 |
| 5,271,900 A | * | 12/1993 | Morita ........................ | 422/80 |
| 5,272,091 A | * | 12/1993 | Egozy et al. ................ | 436/146 |
| 5,292,666 A | * | 3/1994 | Fabinski et al. ............ | 436/114 |
| 5,312,756 A | * | 5/1994 | Jolly ........................... | 436/145 |
| 5,324,666 A | * | 6/1994 | Siepmann et al. .......... | 436/146 |
| 5,340,542 A | * | 8/1994 | Fabinski et al. ......... | 422/82.05 |
| 5,425,919 A | * | 6/1995 | Inoue et al. .................. | 422/67 |
| 5,567,388 A | | 10/1996 | Morita et al. ................. | 422/80 |

FOREIGN PATENT DOCUMENTS

| | | |
|---|---|---|
| DE | 4224077 A1 | 2/1993 |
| JP | 59120954 | 12/1984 |
| JP | 03031761 | 12/1991 |
| WO | WO 93/17333 | 9/1993 |

* cited by examiner

Primary Examiner—Sharidan Carrillo
(74) Attorney, Agent, or Firm—Radar, Fishman & Grauer, PLLC

(57) ABSTRACT

An ultrapure water trap is provided for retaining condensed water of water vapor which is formed in a TC oxidative reaction part, and a passage is so connected that an automatic sample injector can collect ultrapure water from the ultrapure water trap for injecting the same into the TC oxidative reaction part. The automatic sample injector dilutes ordinary pure water which is outside this apparatus with the ultrapure water which is retained in the ultrapure water trap, thereby preparing a test solution having ultralow carbon concentration of not more than 50 ppbC in the interior of a TOC meter.

7 Claims, 4 Drawing Sheets

TOTAL ORGANIC CARBON METER

BACKGROUND OF THE INVENTION

1. Field of the Invention

The present invention relates to a total organic carbon meter for measuring TOC (total organic carbon) or TC (total carbon) in an aqueous sample.

2. Description of the Background Art

In a case of measuring TOC in an aqueous sample with a TOC meter, it is one of important matters that TOC measurement for carbon concentration of not more than 50 ppb (hereinafter referred to as 50 ppbC) is possible in the TOC test method which is defined in the Pharmacopeia of Japan, for example. According to the revised GMP rule enforced on Apr. 1, 1994, medicinal makers must control TOC values of water for injection water and wash water. When a TOC meter is used for the purpose of TOC control, the user must prove that the TOC meter can measure TOC values of not more than 50 ppbC. Following prevalence of the ISO 9000 standard, a TOC meter which is used for controlling TOC in pure water must be capable of measuring TOC values of ultralow concentration also in other fields, similarly to the above.

In order to prove that a TOC meter can measure TOC values of not more than 50 ppbC, it is necessary to prepare a TOC test solution having known concentration of not more than 50 ppbC. However, it is almost impossible for the user to prepare a solution of such low carbon concentration, for the following reasons:

(1) It is difficult to obtain pure water of not more than 50 ppbC itself.

(2) Even if such pure water can be obtained, it is difficult to prepare and keep a test solution having concentration of not more than 50 ppbC in excellent accuracy, due to contamination exerted from the exterior during preparation of the test solution.

SUMMARY OF THE INVENTION

An object of the present invention is to enable a user to prove that a TOC meter has measurement sensitivity for ultralow concentration by enabling preparation of a test solution of ultralow concentration in the interior of the TOC meter.

The TOC meter to which the present invention is directed at least comprises a reaction part at least including a TC oxidative reaction part for converting TC in an aqueous sample to $CO_2$, an automatic sample injector for collecting the aqueous sample or ordinary pure water and injecting the same into the reaction part, a sample injection control part for controlling the sample injecting operation of the automatic sample injector, a carrier gas supply part for supplying carrier gas to the reaction part, a $CO_2$ detection part for detecting $CO_2$ which is received from the reaction part with the carrier gas, and a data processing part for processing a detection signal of the $CO_2$ detection part. According to the present invention, the TOC meter further comprises an ultrapure water trap mechanism which is provided in a passage between the TC oxidative reaction part of the reaction part and the $CO_2$ detection part for retaining condensed water of water vapor which is formed in the TC oxidative reaction part, and a passage for connecting the automatic sample injector with an ultrapure water trap of the ultrapure water trap mechanism to be capable of collecting ultrapure water from the ultrapure water trap and injecting the same into the reaction part. The sample injection control part is also adapted to control an operation of collecting the ultrapure water and ordinary pure water which is outside this apparatus for diluting the ordinary pure water with the ultrapure water and injecting the diluted pure water into the reaction part.

In a preferred mode shown in FIG. 2, the data processing part 13 comprises a calibration curve part 30 for forming and holding calibration curve data, a carbon concentration calculating part 31 for calculating carbon concentration from the detection signal of the $CO_2$ detection part 12 through the calibration curve, and a dilution magnification calculating part 32 for calculating a dilution magnification for forming a test solution having ultralow carbon concentration by diluting the ordinary pure water with the ultrapure water stored in the ultrapure water trap 22 from the concentration calculated by the carbon concentration calculating part 31 in measurement of the ordinary pure water which is outside this apparatus, and the sample injection control part 18 controls to collect the ordinary pure water and the ultrapure water in accordance with the dilution magnification calculated by the dilution magnification calculating part 32 and inject the same into the reaction part 2.

According to the present invention, condensed water of water vapor which is formed in the TC oxidative reaction part is collected in the TOC meter. Since this condensed water is ultrapure water whose TOC value is substantially zero, it is possible to prove that the TOC meter has sensitivity for ultralow concentration by diluting the ordinary pure water (at least 100 ppbC in general), which is subjected to measurement of concentration, with the ultrapure water for preparing a test solution of ultralow concentration and measuring the test solution. Thus, the test solution of ultralow concentration can be prepared in the TOC meter according to the present invention, whereby it is possible to simply measure a test solution of ultralow concentration in high accuracy.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
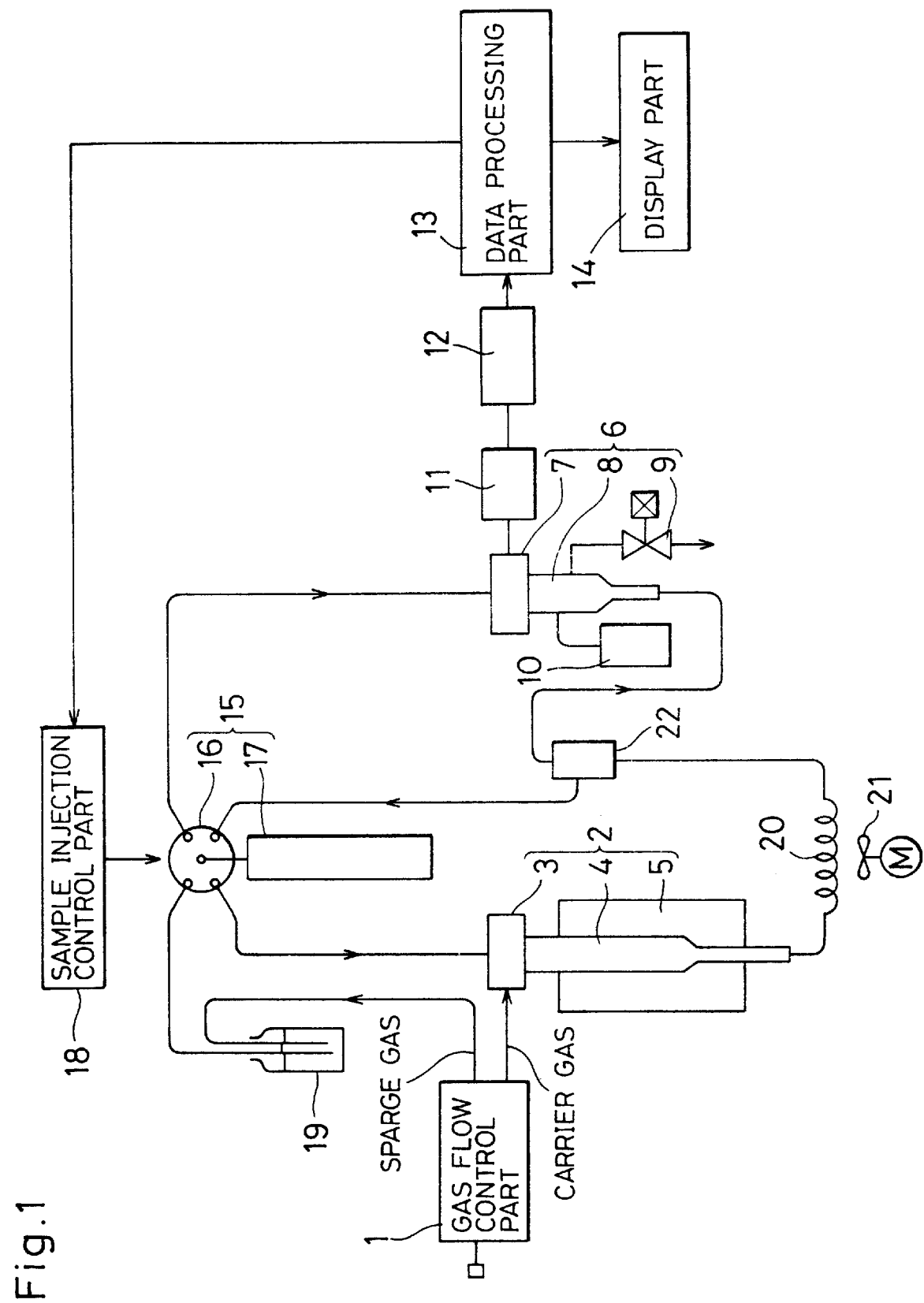
FIG. 1 is a block diagram showing an embodiment of the present invention.
Figure 2:
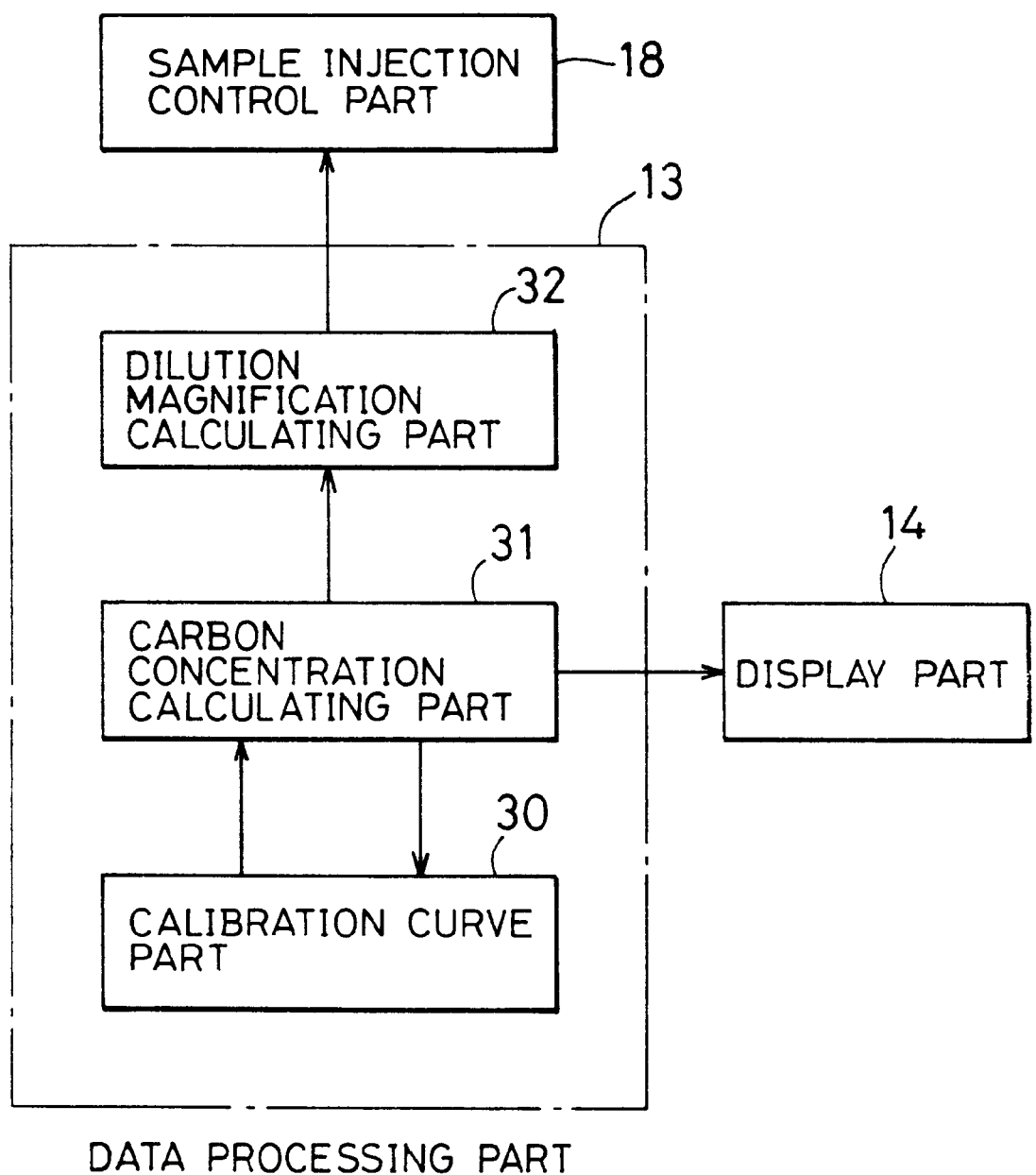
FIG. 2 is a block diagram showing the present invention, illustrating a part corresponding to the present invention among functions of a data processing part shown in FIG. 1.

FIG. 1 shows an embodiment of the present invention.

A TOC meter is provided in its body with a TC oxidative reaction part 2 for converting TC in an aqueous sample to $CO_2$, and an IC reaction part 6 for converting IC (inorganic carbon) in the aqueous sample to $CO_2$. An automatic sample injector 15 comprising a four-port valve 16 and a microsyringe 17 is provided for collecting the aqueous sample by a constant volume and guiding the same to the TC oxidative reaction part 2 or the IC reaction part 6. The TC oxidative reaction part 2 and the IC reaction part 6 are connected to the microsyringe 17 through the four-port valve 16, while a TOC meter sample container 19 is also connected to the four-port valve 16. The microsyringe 17 collects a constant volume of ordinary pure water such as ion exchanged water or the aqueous sample from the sample container 19, for guiding the same to the TC oxidative reaction part 2 or the IC reaction part 6.

The TC oxidative reaction part 2 is provided with a TC combustion tube 4 which is filled up with an oxidation catalyst, and a heating furnace 5 is provided around the TC combustion tube 4 for heating the same. The aqueous sample is injected into the TC combustion tube 4 through a TC sample injection port 3 thereof. Further, a passage for carrier gas from a gas flow control part 1 is connected to the TC sample injection port 3, so that pure gaseous oxygen or oxygen-containing gas such as high purity air from which a carbon component is removed, for example, is supplied from the gas flow control part 1 to the TC combustion tube 4 through the TC sample injection port 3. An outlet of the TC oxidative reaction part 2 is connected to dehumidifying/dedusting part 11 through a cooling coil 20, an ultrapure water trap 22 for blank check and the IC reaction part 6, as well as to a $CO_2$ detection part 12 of an NDIR (non-dispersive infrared spectrophotometer) through the dehumidifying/dedusting part 11.

A sparge gas passage is guided from the gas flow control part 1 to the sample container 19 to be capable of guiding the gas from the gas flow control part 1 also into the sample container 19 as sparge gas, so that IC can be removed from the ordinary pure water or the aqueous sample stored in the sample container 19.

The IC reaction part 6 is provided with an IC reactor 8 which is filled up with an IC reaction solution, so that a liquid sample is injected from the automatic sample injector 15 through an IC sample injection port 7. In the IC reactor 8, IC in the injected liquid sample is generated as $CO_2$, and guided to the $CO_2$ detection part 12 through the dehumidifying/dedusting part 11 by the carrier gas which is supplied through the TC oxidative reaction part 2. Numeral 10 denotes an IC reaction solution supplier for supplying the IC reaction solution to the IC reactor 8, and numeral 9 denotes a drain valve for discharging the IC reaction solution from the IC reactor 8.

The cooling coil 20 which is provided in the passage between the TC oxidative reaction part 2 and the IC reaction part 6 is adapted to cool the gas from the TC oxidative reaction part 2, and a fan 21 is provided for air-cooling the coil 20. The ultrapure water trap 22 which is provided downstream the coil 20 is adapted to condense water vapor which is formed in the TC oxidative reaction part 2 and retaining the same. A passage for the ultrapure water which is retained in the ultrapure water trap 22 is connected to one port of the four-port valve 16, so that the ultrapure water can be collected by the microsyringe 17 for sample injection and injected into the TC oxidative reaction part 2.

Description is now made on an operation for forming a calibration curve and an operation for proving that this TOC meter has sensitivity for ultralow concentration such as that of not more than 50 ppbC in this embodiment.

Figure 3A:
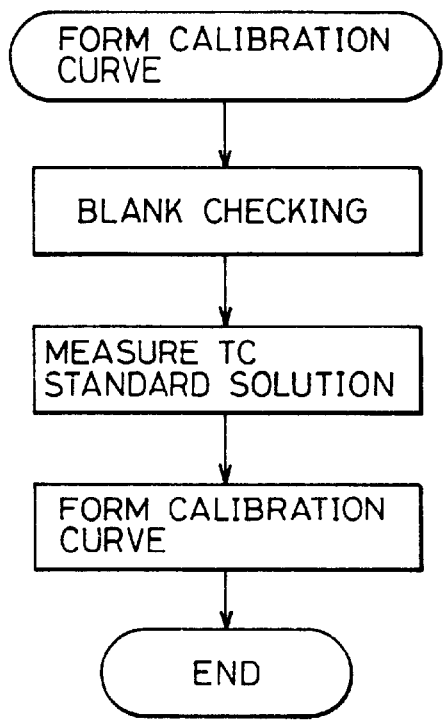
FIG. 3A is a flow chart showing a calibration curve forming operation in the embodiment.

FIG. 3A shows the calibration curve forming operation. Ordinary pure water is introduced into the sample container 19, for forming blank check ultrapure water which is required for a blank check. The ordinary pure water contains TOC of at least 100 ppbC in general. When the ordinary pure water is injected into the TC oxidative reaction part 2 by the automatic sample injector 15, water vapor is formed in the TC oxidative reaction part 2, and the ultrapure water trap 22 retains ultrapure water resulting from condensation of the water vapor. The automatic sample injector 15 collects the ultrapure water which is retained in the ultrapure water trap 22 by a constant volume and injects the same into the TC oxidative reaction part 2, for carrying out a blank check. The ultrapure water which is retained in the ultrapure water trap 22 can be regarded as containing substantially zero TOC. Due to this blank check, it is confirmed that the apparatus has a sufficiently low blank value.

Figure 3B:
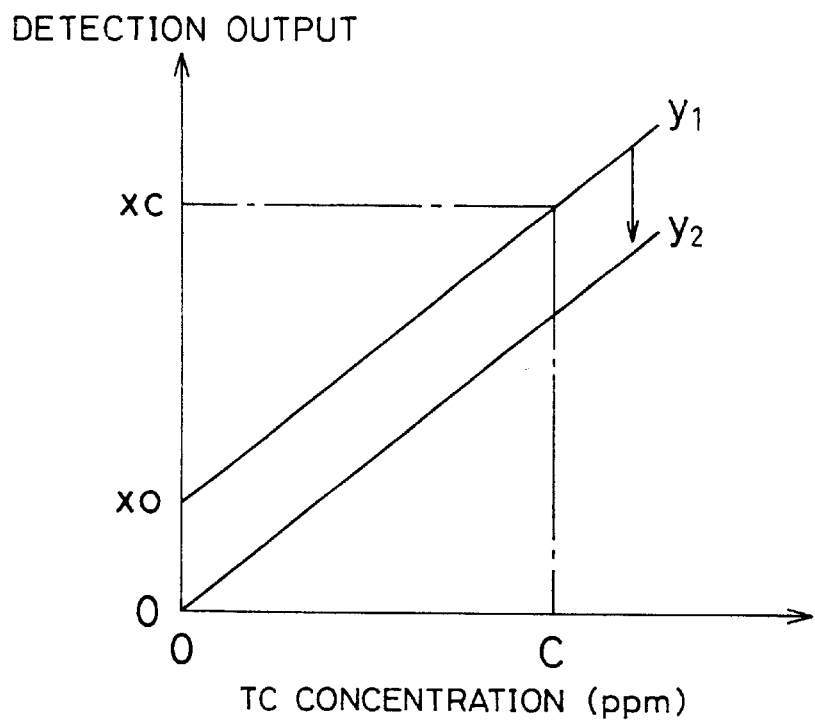
FIG. 3B illustrates the calibration curve forming operation in the embodiment.

Then, TC standard solutions are measured. The standard solutions are prepared from those having TC concentration values of zero and C ppm respectively, for example. It is assumed that detection outputs for the standard solutions having concentration values of zero and C ppm are $x_0$ and xc respectively. The value $x_0$ is not zero, since ordinary pure water forming the standard solution generally contains TOC of at least 100 ppbC. When a straight line $y_1$ connecting measured values of the two reference solutions is so translated that $x_0$ is zero for forming a straight line $y_2$ as shown in FIG. 3B, this straight line $y_2$ defines a calibration curve. The data of the calibration curve are held in a calibration curve part 30.

Figure 4:
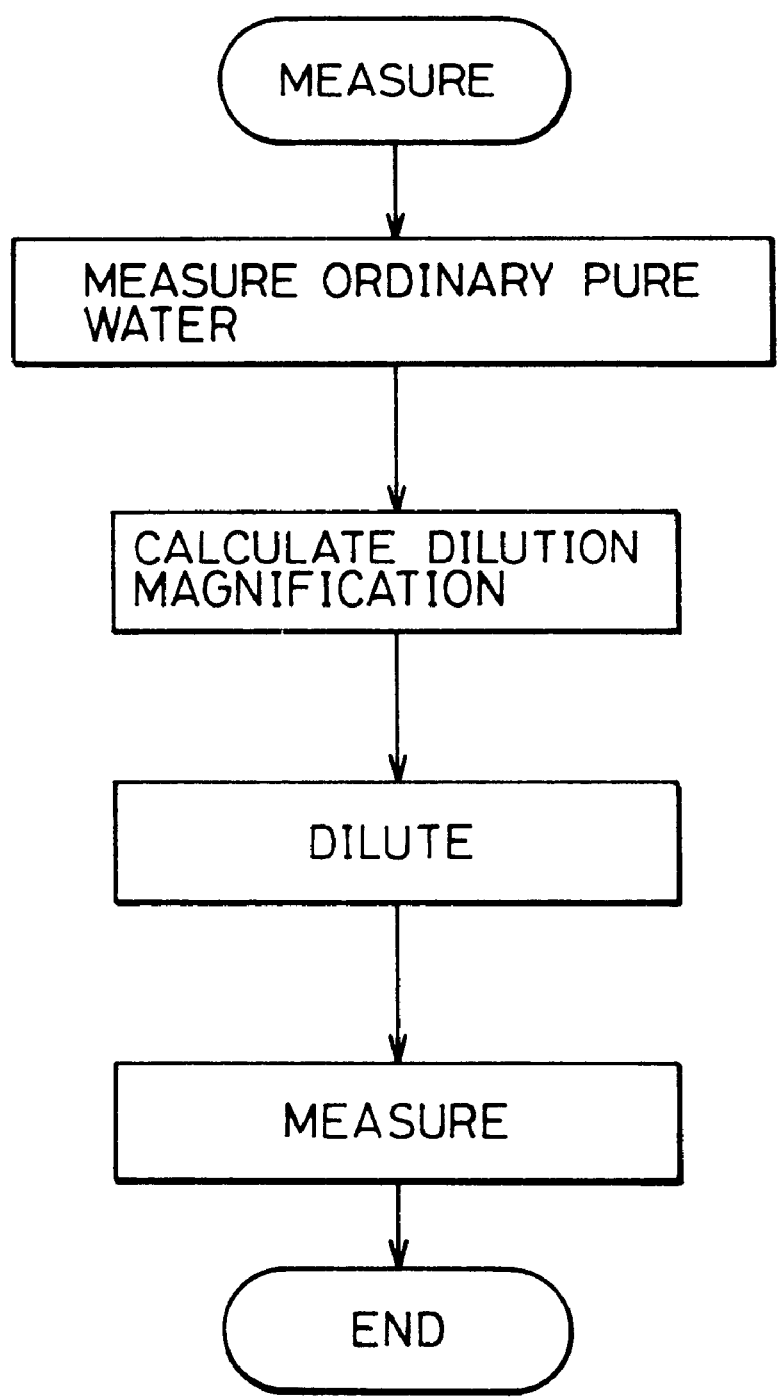
FIG. 4 is a flow chart showing a measuring operation for confirming that the embodiment has sensitivity for ultralow concentration.

Then, it is proved that this TOC meter has sensitivity for not more than 50 ppbC, with reference to FIG. 4.

The ordinary pure water is introduced into the sample container 19, so that the same is injected into the TC oxidative reaction part 2 by a constant volume, to be subjected to measurement. A data processing part 13 calculates TC concentration of the ordinary pure water, on the basis of the detection value upon measurement of the ordinary pure water and the calibration curve which is held in the calibration curve part 30. Then, a dilution magnification for diluting the ordinary pure water with the ultrapure water which is retained in the ultrapure water trap 22 so that its concentration reaches a previously set value of not more than 50 ppbC is calculated from the TC concentration as calculated. Assuming that the previously set concentration of the test solution is 40 ppbC and the TC concentration obtained by measuring the ordinary pure water is 200 ppbC, for example, the dilution magnification is 5 times. Volumes of the ordinary pure water and the ultrapure water to be collected are calculated from the result as calculated. The microsyringe 17 collects the ultrapure water from the ultrapure water trap 22 by the calculated volume, and then collects the ordinary pure water from the sample container 19 also by the calculated volume. Assuming that the ordinary pure water is collected by 400 μl and the ultrapure water is collected by 1600 μl, for example, $$200\ ppbC \times (400/(400+1600)) = 40\ ppbC$$

and hence a test solution of 40 ppbC is prepared in the TOC meter with the ordinary pure water of 200 ppbC.

Then, the test solution which is prepared in 40 ppbC, for example, is injected into the TC oxidative reaction part 2 from the automatic sample injector 15 so that its concentration is obtained by TC measurement, thereby confirming that TC measurement of not more than 50 ppbC is possible.

TC measurement is carried out in the aforementioned embodiment. In order to strictly prove that TOC measurement of not more than 50 ppbC is possible, on the other hand, ordinary pure water which is used for preparing a test solution of not more than 50 ppbC may be introduced into the sample container 19 so that inert gas such as nitrogen gas is fed from the sparge gas passage communicating with the gas flow control part 1, thereby previously removing IC from the ordinary pure water. Thus, only TOC remains with removal of IC, so that it is possible to confirm that low concentration TOC measurement is possible.

Although the present invention has been described and illustrated in detail, it is clearly understood that the same is by way of illustration and example only and is not to be taken by way of limitation, the spirit and scope of the present invention being limited only by the terms of the appended claims.

We claim:

1. A total organic carbon meter comprising a reaction part at least including a TC oxidative reaction part for converting total carbon in an aqueous sample to $CO_2$, an automatic sample injector for collecting said aqueous sample or ordinary pure water and injecting the same into said reaction part, a sample injection control part for controlling the sample injecting operation of said automatic sample injector, a carrier gas supply part for supplying pure gaseous oxygen or oxygen-containing gas to said reaction part as carrier gas, a $CO_2$ detection part for detecting said $CO_2$ being received from said reaction part with said carrier gas, and a data processing part for processing a detection signal of said $CO_2$ detection part, said total organic carbon meter further comprising:
  an ultrapure water trap mechanism being provided in a passage between said TC oxidative reaction part of the reaction part and said $CO_2$ detection part for retaining condensed water of water vapor being formed in said TC oxidative reaction part; and
  a passage for connecting said automatic sample injector with an ultrapure water trap of said ultrapure water trap mechanism to be capable of collecting ultrapure water from said ultrapure water trap and injecting the same into said reaction part,
  said sample injection control part also controlling an operation of collecting said ultrapure water and ordinary pure water being outside this apparatus and diluting said ordinary pure water with said ultrapure water for preparing a test solution having ultralow carbon concentration and injecting the same into said reaction part,
  wherein said data processing part comprises a calibration curve part for forming and holding calibration curve data, a carbon concentration calculating part for calculating carbon concentration from said detection signal of said $CO_2$ detection part through said calibration curve. and a dilution magnification calculating part for calculating a dilution magnification for forming a test solution having ultralow carbon concentration by diluting said ordinary pure water with said ultrapure water of said ultrapure water trap from said concentration being calculated by said carbon concentration calculating part in measurement of said ordinary pure water being outside this apparatus, and
  wherein said sample injection control part controls to collect said ordinary pure water and said ultrapure water in accordance with said dilution magnification being calculated by said dilution magnification calculating part and inject the same into said TC oxidative reaction part.

2. The total organic carbon meter in accordance with claim 1, further comprising an IC reaction part for converting inorganic carbon in said aqueous sample to $CO_2$,
  said automatic sample injector being connected also with said IC reaction part by a passage, to be capable of collecting said aqueous sample and injecting the same also into said IC reaction part.

3. The total organic carbon meter in accordance with claim 1, wherein
  said ultrapure water trap mechanism also includes a cooling coil being arranged between said reaction part and said ultrapure water trap for cooling said gas from said reaction part and a fan for cooling said cooling coil, in addition to said ultrapure water trap for condensing said water vapor being formed in said reaction part and retaining the same.

4. The total organic carbon meter in accordance with claim 1, wherein
  said automatic sample injector comprises a microsyringe and a passage switching valve for switching to connect said microsyringe to between a sample container for said aqueous sample, said ultrapure water trap and said reaction part.

5. The total organic carbon meter in accordance with claim 1, wherein
  said reaction part is provided with a TC combustion tube being filled up with an oxidation catalyst, a heating furnace being provided around said TC combustion tube for heating the TC combustion tube.

6. The total organic carbon meter in accordance with claim 1, wherein
  a dehumidifying/dedusting part is arranged on an inlet passage for said $CO_2$ detection part.

7. The total organic carbon meter in accordance with claim 1, wherein
  a passage for guiding sparge gas is provided to a sample container storing said aqueous sample or said pure water, for removing inorganic carbon from said aqueous sample or said ordinary pure water.

* * * * *